(12) United States Patent
De Nucci

(10) Patent No.: US 10,280,162 B2
(45) Date of Patent: May 7, 2019

(54) PYRIDOPYRIMIDINES DERIVATIVES COMPOUNDS

(71) Applicant: BIOLAB SANUS FARMACEUTICA LTDA, Taboão da Serra (BR)

(72) Inventor: Gilberto De Nucci, São Paulo (BR)

(73) Assignee: BIOLAB SANUS FARMACEUTICA LTDA, Taboao da Serra (BR)

( * ) Notice: Subject to any disclaimer, the term of this patent is extended or adjusted under 35 U.S.C. 154(b) by 0 days.

(21) Appl. No.: 14/851,072

(22) Filed: Sep. 11, 2015

(65) Prior Publication Data

US 2016/0075702 A1 Mar. 17, 2016
US 2018/0111926 A2 Apr. 26, 2018

Related U.S. Application Data

(60) Provisional application No. 62/049,506, filed on Sep. 12, 2014.

(51) Int. Cl.
*C07D 471/04* (2006.01)

(52) U.S. Cl.
CPC .................. *C07D 471/04* (2013.01)

(58) Field of Classification Search
CPC .................................................. C07D 471/04
See application file for complete search history.

(56) References Cited

FOREIGN PATENT DOCUMENTS

| WO | 2002000657 A2 | 1/2002 |
|----|---------------|--------|
| WO | 2002018380 A1 | 3/2002 |
| WO | 2008008704 A2 | 1/2008 |
| WO | 2013183016 A1 | 12/2013 |

OTHER PUBLICATIONS

Tanifum, et al., Novel pyridopyrimidine derivatives as inhibitors of stable toxin a (STa) induced cGMP synthesis, Bioorganic & Medicinal Chemistry Letters 19, 3067-3071 (2009).*
International Preliminary Examination Report on Patentability, International Application No. PCT/BR2015/050147.
A. Y. Kots et al: "From the Cover: Pyridopyrimidine derivatives as inhibitors of cyclic nucleotide synthesis: Application for treatment of diarrhea", Proceedings of the National Academy of Sciences, vol. 105, No. 24, Jun. 17, 2008 (Jun. 17, 2008), pp. 8440-8445, XP055054213, ISSN: 0027-8424, DOI: 10.1073/pnas.0803096105.
Database Pubchem [Online] NIH; Sep. 13, 2005 (Sep. 13, 2005), "5-(1,3-benzodioxol-5-yl)-1,3-dimethyl-5,11-dihydro-1H-indeno-[2',1':5,6] pyrido[2,3-d]pyrimidine-2,4,6-trione" XP002756100,accession No. 4113185 Database accession No. 4113185.
Database Registry [Online] Chemical Abstracts Service, Columbus, Ohio, US; Sep. 2, 2003 (Sep. 2, 2003), "1H-Indeno[2',1':5,6]pyrido[2,3-d]pyrimidine-2,4,6(3H)-trione, 5-(5-bromo-2-fluorophenyl)-5,11-dihydro-1,3-dimethyl" XP002756142,accession No. 577698-51-2 Database accession No. 577698-51-2.

Database Registry [Online], Chemical Abstracts Service, Columbus, Ohio, US; Apr. 2, 2006 (Apr. 2, 2006), "1H-Indeno[2',1':5,6]pyrido[2,3-d]pyrimidine-2,4,6(3H)-trione, 5,11-dihydro-5-(3-methoxy-4-(Apr. 2, 2006), 37 1H-Indeno[2',1':5,6]pyrido[2,3-d]pyrimidine-2,4,6(3H)-trione, 5,11-dihydro-5-(3-methoxy-4-propoxphenyl)-1,3-dimethyl-" XP002756144,accession No. 878990-96-6 Database accession No. 878990-96-6.
Database Registry [Online] Chemical Abstracts Service, Columbus, Ohio, US; Mar. 20, 2006 (Mar. 20, 2006), "1H-Indeno[2',1':5,6]pyrido[2,3-d]pyrimidine-2,4,6(3H)-trione, 5-(3-ethoxyphenyl)-5,11-dihydro-1,3-dimethyl-" XP002756145,accession No. 878438-82-5 Database accession No. 878438-82-5.
Database Registry [Online] Chemical Abstracts Service, Columbus, Ohio, US; Aug. 7, 2006 (Aug. 7, 2006), "1H-Indeno[2',1':5,6]pyrido[2,3-d]pyrimidine-2,4,6(3H)-trione, 5-(4-ethoxyphenyl)-5,11-dihydro-1,3-dimethyl-" XP002756147,accession No. 899405-34-6 Database accession No. 899405-34-6.
Database Registry [Online] Chemical Abstracts Service, Columbus, Ohio, US; Jul. 12, 2006 (Jul. 12, 2006), "1H-Indeno[2',1:5,6]pyrido[2,3-d]pyrimidine-2,4,6(3H)-trione, 5-(3,4-dimethoxyphenyl)-5,11-dihydro-1,3-dimethyl-", XP002756150,accession No. 892160-49-5 Database accession No. 892160-49-5.
Database Registry [Online] Chemical Abstracts Service, Columbus, Ohio, US; Dec. 20, 2001 (Dec. 20, 2001),"1H-Indeno[2',1':5,6]pyrido[2,3-d]pyrimidine-2,4,6(3H)-trione, 5-(2,3-dimethoxyphenyl)-5,11-dihydro-1,3-dimethyl-", XP002756152,accession No. 377059-05-7 Database accession No. 377059-05-7.

(Continued)

*Primary Examiner* — Erich A Leeser

(74) *Attorney, Agent, or Firm* — Reed Smith LLP; Matthew P. Frederick; Ryan P. Cox

(57) ABSTRACT

The present invention describes new pyridopyrimidine derivatives compounds with structure represented by General Formula (I):

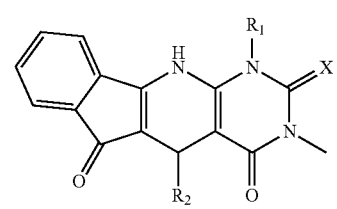

General Formula (I)

or pharmaceutically acceptable salts thereof, or their mixtures (in any ratio), a pharmaceutical composition containing them, a method for using the new pyridopyrimidine derivatives compounds as inhibitor of the cyclic nucleotide synthesis or as inhibitor of the cAMP and cGMP synthesis, and their uses in the prophylactic and/or curative treatment of diarrhea, colitis and irritable bowel syndrome.

13 Claims, 5 Drawing Sheets

(56) References Cited

OTHER PUBLICATIONS

Database Registry [Online] Chemical Abstracts Service, Columbus, Ohio, US; Apr. 26, 2001 (Apr. 26, 2001), "1H-Indeno[2',1':5,6]pyrido[2,3-d]pyrimidine-2,4,6(3H)-trione, 5-(2,5-dimethoxyphenyl)-5,11-dihydro-1,3-dimethyl-", XP002756154,accession No. 332937-82-3 Database accession No. 332937-82-3.

Database Registry [Online] Chemical Abstracts Service, Columbus, Ohio, US; Jul. 12, 2006 (Jul. 12, 2006), "1H-Indeno[2',1':5,6]pyrido[2,3-d]pyrimidine-2,4,6(3H)-trione, 5-(2,3- dichlorophenyl)-5,11-dihydro-1,3-dimethyl-", XP002756155,accession No. 892183-70-9 Database accession No. 892183-70-9.

Database Registry [Online] Chemical Abstracts Service, Columbus, Ohio, US; Dec. 13, 2001 (Dec. 13, 2001), "1H-Indeno[2',1':5,6]pyrido[2,3-d]pyrimidine-2,4,6(3H)-trione, 5-(2,4-dichlorophenyl)-5,11-dihydro-1,3-dimethyl-", XP002756158,accession No. 374921-25-2 Database accession No. 374921-25-2.

Database Registry [Online] Chemical Abstracts Service, Columbus, Ohio, US; Mar. 5, 2001 (Mar. 5, 2001), "1H-Indeno[2',1':5,6]pyrido[2,3-d]pyrimidine-2,4,6(3H)-trione, 5-(3,4-dichlorophenyl)-5,11-dihydro-1,3-dimethyl-", XP002756161,accession No. 325747-03-3 Database accession No. 325747-03-3 Database accenssion no. 325747-03-3.

Database Registry [Online] Chemical Abstracts Service, Columbus, Ohio, US; Aug. 27, 2001 (Aug. 27, 2001), "1H-Indeno[2',1':5,6]pyrido[2,3-d]pyrimidine-2,4,6(3H)-trione, 5,11-dihydro-1,3-dimethyl-5-(3,4,5-trimethoxyphenyl)", XP002756169,accession No. 352659-15-5 Database accession No. 352659.

Toropov et al., "QSAR models for inhibitors of physiological impact of *Escherichia coli*that leads to diarrhea" Biochemical and Biophysical Research Communications 432 (2013) 214-225.

\* cited by examiner

PYRIDOPYRIMIDINES DERIVATIVES COMPOUNDS

This application claims benefit of U.S. Provisional Application No. 62/049,506, filed Sep. 12, 2014, which is herein incorporated by reference in its entirety.

FIELD OF THE INVENTION

The present invention describes new pyridopyrimidine derivatives compounds, or pharmaceutically acceptable salts thereof, or their mixtures (in any ratio), a pharmaceutical composition containing them, a method for using the new pyridopyrimidine derivatives compounds as inhibitor of the cyclic nucleotide synthesis, a method for using the new pyridopyrimidine derivatives compounds as inhibitor of the cAMP and cGMP synthesis, and their uses in the prophylactic and/or curative treatment of diarrhea, colitis and irritable bowel syndrome.

BACKGROUND OF THE INVENTION

According to the United Nations Children's Fund (UNICEF) and the World Health Organization (WHO), diarrhea disease is the second leading cause of death and a main cause of malnutrition in children under five years old. A significant proportion of diarrhea disease can be prevented through safe drinking-water and adequate sanitation and hygiene.

Diarrhea is characterized by an increase in the frequency of bowel movements compared to normal bowel movement or a decrease in the formation of a stool. Although changes in frequency of bowel movements and looseness of stools can vary independently of each other, changes often occur in both.

In most cases, diarrhea signs and symptoms usually last a couple of days. But sometimes diarrhea can last for weeks. In these situations, diarrhea can be a sign of a serious disorder, such as inflammatory bowel disease, or a less serious condition, such as irritable bowel syndrome.

Diarrhea can be an infectious bacterial or viral disorder caused by parasites. The diarrhea may also be a non-infectious diarrhea caused by food poisoning, food additives, food allergies, malabsorption syndromes (like gluten or lactose intolerance), antibiotic therapies, diseases of the intestines (Crohn's disease, ulcerative colitis), etc. Typical treatment is to give fluids to prevent dehydration and continued feeding while administering drugs for the underlying cause.

In cases of infectious disorder caused by bacteria, the pathogenic mechanisms of *Escherichia coli* (a gram-negative bacteria), that induced diarrhea, probably involves secretion of a heat stable toxin (STa).

Thus, the present inventor's efforts to develop new pyridopyrimidine derivative compounds inhibitors of cyclic nucleotide synthesis caused by stable toxin of *Escherichia coli* (STa). The STa induces diarrhea when it binds to intestinal epithelial cell membrane receptor, guanylyl cyclase type C (GC-C). This activates the enzyme to convert guanosine triphosphate (GTP) to cyclic guanosine 3',5'-monophosphate (cGMP), causing intracellular levels of cGMP to spike. This in turn induces activation of a cGMP-dependent protein kinase and chloride-ion channel, cystic fibrosis transmembrane conductance regulator (CFTR). Activation of CFTR triggers the flux of chloride ions into the intestinal lumen and the accumulation of water and sodium ions, thus causing diarrhea.

International Publication No. WO 2008/008704 describes inhibitors of cyclic nucleotide synthesis and their use for therapy of various diseases.

Another class of inhibitor of the cAMP and cGMP synthesis and inhibitor of cyclic nucleotide synthesis is described in the publication by TANIFUM [E. A. TANIFUM et al., "Novel pyridopyrimidine derivatives as inhibitors of stable toxin a (STa) induced cGMP synthesis". Bioorganic & Medicinal Chemistry Letters, 2009, 19:3067-3071]. According to this publication, one of the best compounds identified was Compound 24 (FPIPP), with the following structural form:

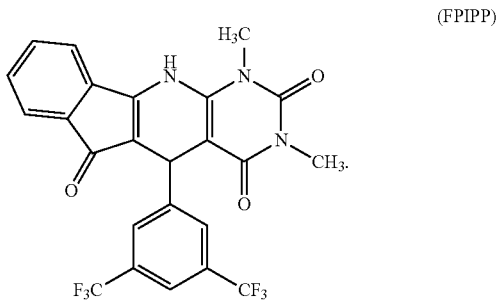 [SMILES: Cn1c2c(c(=O)n(C)c1=O)C(c1cc(C(F)(F)F)cc(C(F)(F)F)c1)C1=C(N2)c2ccccc2C1=O]

(FPIPP)

Also according to TANIFUM [E. A. TANIFUM et al., "Novel pyridopyrimidine derivatives as inhibitors of stable toxin a (STa) induced cGMP synthesis". Bioorganic & Medicinal Chemistry Letters, 2009, 19:3067-3071], the development of drugs that are effective against the physiological mechanisms that cause the imbalance of fluids in the intestine would be a significant addition in therapeutic arsenal.

Based on the above, the inventor of the present invention developed new compounds, new derivatives of pyridopyrimidine, that can be used in treatment, prevention or amelioration of symptoms of diarrhea.

DESCRIPTION OF THE INVENTION

The main objective of the present invention is to provide new pyridopyrimidine derivative compounds with a structure represented by General Formula (I):

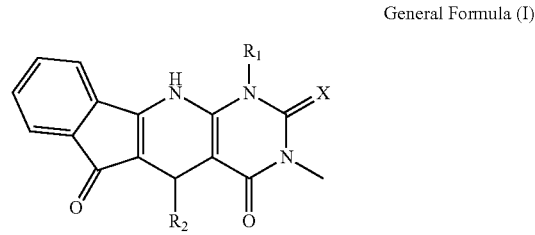

General Formula (I)

or pharmaceutically acceptable salts thereof, or their mixtures (in any ratio), a pharmaceutical composition containing them, a method for using the new pyridopyrimidine derivatives compounds as inhibitor of the cyclic nucleotide synthesis, a method for using the new pyridopyrimidine derivatives compounds as inhibitor of the cAMP and cGMP synthesis, and their uses in the prophylactic and/or curative treatment of diarrhea, colitis and irritable bowel syndrome.

In some aspects, the present invention provides pharmaceutical compositions comprising as active ingredient an effective amount of the new pyridopyrimidine derivative compounds, or pharmaceutically acceptable salts thereof, or their mixtures (in any ratio), and pharmaceutically acceptable excipients.

Another objective of the present invention is the use of the new pyridopyrimidine derivative compounds, their pharmaceutically acceptable salts or mixtures thereof (in any ratio), for inhibiting the cyclic nucleotide synthesis. Furthermore, it is the objective of the present invention the use of one of the new pyridopyrimidine derivative compounds, their pharmaceutically acceptable salts or mixtures thereof (in any ratio), for inhibiting the cAMP and cGMP synthesis.

It is also the objective of the present invention the use of one of the new pyridopyrimidine derivative compounds, their pharmaceutically acceptable salts or mixtures thereof (in any ratio), in the prophylactic and/or curative treatment of diarrhea, colitis and irritable bowel syndrome.

DETAILED DESCRIPTION OF THE INVENTION

Figure 1:
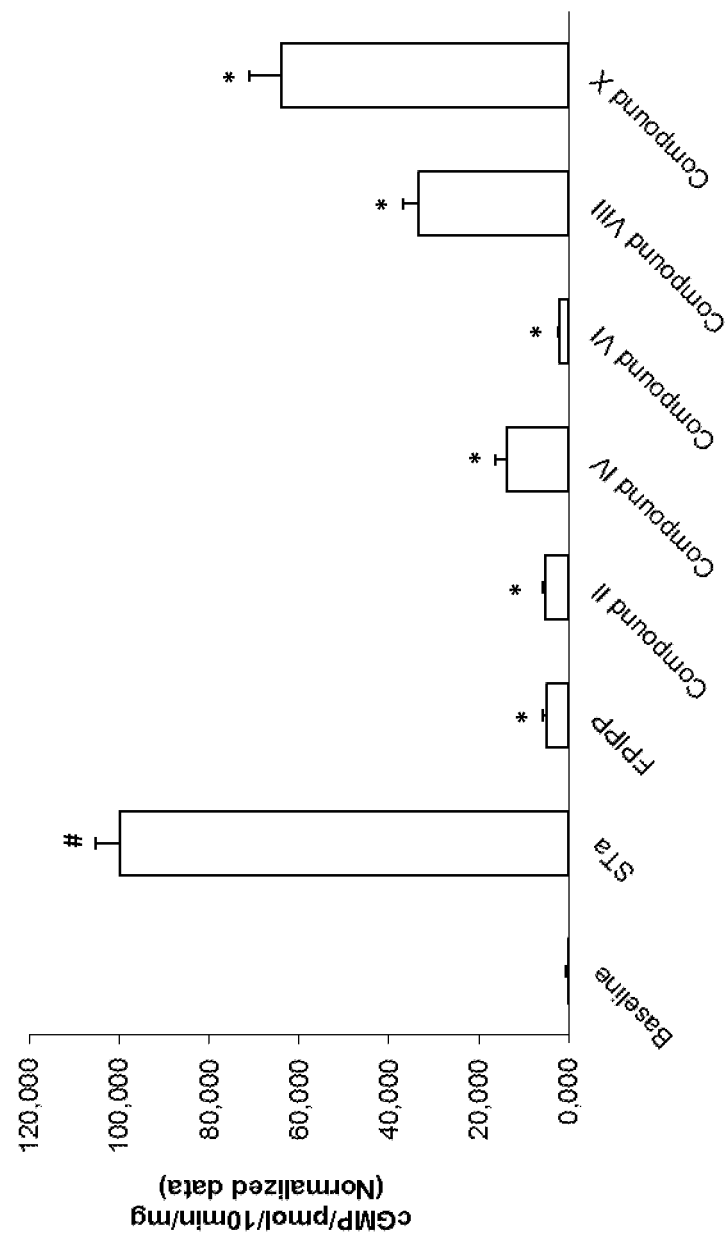
FIG. 1: Effect of Compounds II, IV, VI, VIII and X on cGMP accumulation induced by STa (1 μM) in $T_{84}$ cells.

The present invention describes new pyridopyrimidine derivative compounds with a structure represented by General Formula (I):

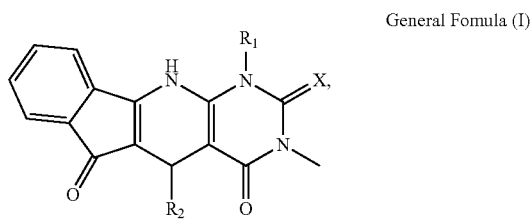

General Formula (I)

or pharmaceutically acceptable salts thereof, or their mixtures (in any ratio), wherein:

$R_1$ is selected from the group consisting of $C_{1-6}$ alkyl, amino $C_{1-6}$ alkyl, dimethylamino $C_{1-6}$ alkyl, halo $C_{1-6}$ alkyl, guanidino $C_{1-6}$ alkyl, and mercapto $C_{1-6}$ alkyl;

$R_2$ is selected from the group consisting of 4-(trifluoromethyl)thiophene, 3-fluoro-5-trifluoromethylphenyl, 3,5-bis-trifluoromethylphenyl, 1,3-benzodioxol-4-yl, 1,3-benzodioxol-5-yl, 2,1,3-benzothiadiazol-4-yl, 2,1,3-benzothiadiazol-5-yl, and substituted aryl wherein the substituent is selected from the group consisting of $C_{1-6}$ alkoxy, halogen, $C_{1-6}$ heteroaralkyl or $C_{2-6}$ heteroaralkenyl; and X is selected from the group consisting of , S and Se.

As used above, and throughout this disclosure, the following terms, unless otherwise indicated, shall be understood to have the following meanings:

The term "alkyl" represents straight, branched or cyclic alkyl chains, for example, the $C_{1-6}$ alkyl group can be methyl, ethyl, propyl, n-propyl, isopropyl, n-butyl, iso-butyl, sec-butyl, tert-butyl, pentyl, hexyl, etc.

The term "alkenyl" includes alkenyl groups of straight, branched or cyclic chains, such as, allyl, benzyl, vinyl, styryl, indolyl, etc. The term "acylamino" represents any acyl derivative of an amino group, such as acetamido, benzamido, etc.

The term "aryl" refers to any functional group or substituent derived from an aromatic ring, for example, phenyl, naphtyl, thienyl, indolyl, etc.

The term "halogen or halo" represents atoms of fluorine, chlorine, bromine or iodine.

The term "patient" is a human or non-human mammal. In one embodiment, a patient is a human. In another embodiment, a patient is a non-human mammal, including, but not limited to, a monkey, dog, cat, baboon, rhesus, mouse, rat, horse, rabbit, cow, etc.

The term "effective amount" as used herein, refers to an amount of a new pyridopyrimidine derivatives compounds, or a pharmaceutical composition thereof that is effective in producing the desire therapeutic, ameliorative, inhibitory or preventive effect when administered to a patient suffering from a condition.

In a preferred embodiment, the compounds of this invention have a structure represented in General Formula (I), or pharmaceutically acceptable salts thereof, or their mixtures (in any ratio), wherein:

$R_1$ is a $C_{1-6}$ alkyl selected from the group consisting of methyl, ethyl, propyl, n-propyl, isopropyl, n-butyl, iso-butyl, sec-butyl, tert-butyl, pentyl, and hexyl;

$R_2$ is selected from the group consisting of: 4-(trifluoromethyl)thiophene, 3-fluoro-5-trifluoromethylphenyl, 3,5-bis-trifluoromethylphenyl, 1,3-benzodioxol-4-yl, 1,3-benzodioxol-5-yl, 2,1,3-benzothiadiazol-4-yl, and 2,1,3-benzothiadiazol-5-yl; and X represents O or S.

In a more preferred embodiment, the compounds of this invention have a structure represented in General Formula (I), or pharmaceutically acceptable salts thereof, or their mixtures (in any ratio), wherein:

$R_1$ is methyl or ethyl;

$R_2$ is selected from the group consisting of: 4-(trifluoromethyl)thiophene, 3-fluoro-5-trifluoromethylphenyl, 3,5-bis-trifluoromethylphenyl, 1,3-benzodioxol-4-yl, 1,3-benzodioxol-5-yl, 2,1,3-benzothiadiazol-4-yl, and 2,1,3-benzothiadiazol-5-yl; and X is O or S.

In particular, preferred compounds are the compounds of General formula (I) described in the examples as individual compounds, as well as pharmaceutically acceptable salts thereof. Preferred substituents are those of the specific examples described in TABLE 1.

TABLE 1

General Formula (I)

[Structure: indeno-pyrido-pyrimidine core with R1 on N, X double-bonded, methyl on N, R2 substituent]

| Comp. | R₁ | R₂ | X | Formula | m.p. | Mol Wt |
|---|---|---|---|---|---|---|
| I | Methyl | 4-(trifluoromethyl)thiophene | O | $C_{21}H_{14}F_3N_3O_3S$ | 265° C. | 445.07 |
| II | Methyl | 4-(trifluoromethyl)thiophene | S | $C_{21}H_{14}F_3N_3O_2S_2$ | 178° C. | 461.05 |
| III | Methyl | 3-fluoro-5-trifluoromethylphenyl | S | $C_{23}H_{15}F_4N_3O_2S$ | 313° C. | 473.08 |
| IV | Ethyl | 3-fluoro-5-trifluoromethylphenyl | O | $C_{24}H_{17}F_4N_3O_3$ | 177° C. | 471.12 |
| V | Methyl | 3,5-bistrifluoromethylphenyl | S | $C_{24}H_{15}F_6N_3O_2S$ | 314° C. | 523.08 |

TABLE 1-continued

General Formula (I)

| | | Structure Data | | | | |
|---|---|---|---|---|---|---|
| Comp. | R₁ | R₂ | X | Formula | m.p. | Mol Wt |
| VI | Ethyl | 3,5-bistrifluoro-methylphenyl | O | $C_{25}H_{17}F_6N_3O_3$ | 166° C. | 521.12 |
| VII | Methyl | 1,3-benzodioxol-4-yl | O | $C_{23}H_{17}N_3O_5$ | 300° C. | 415.12 |
| VIII | Methyl | 1,3-benzodioxol-4-yl | S | $C_{23}H_{17}N_3O_4S$ | 310° C. | 431.09 |
| IX | Methyl | 1,3-benzodioxol-5-yl | O | $C_{23}H_{17}N_3O_5$ | 338° C. | 415.12 |
| X | Methyl | 2,1,3-benzothia-diazol-4-yl | O | $C_{22}H_{15}N_5O_3S$ | 331° C. | 429.09 |
| XI | Methyl | 2,1,3-benzothia-diazol-5-yl | O | $C_{22}H_{15}N_5O_3S$ | 358° C. | 429.09 |

TABLE 1-continued

General Formula (I)

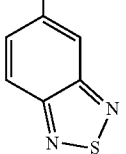

Structure Data

| Comp. | R$_1$ | R$_2$ | X | Formula | m.p. | Mol Wt |
|---|---|---|---|---|---|---|
| XII | Methyl | 2,1,3-benzothiadiazol-5-yl | S | C$_{22}$H$_{15}$N$_5$O$_2$S$_2$ | 362° C. | 445.07 |

Preferred compounds of General formula (I) are those selected from the group consisting of:

Compound I: (5-(4-trifluoromethylthiophen)-1,3-dimethyl-5,11-dihydro-1H-indeno-[2',1':5,6]pyrido[2,3-d]pyrimidine-2,4,6-trione, which Chemical Structure is:

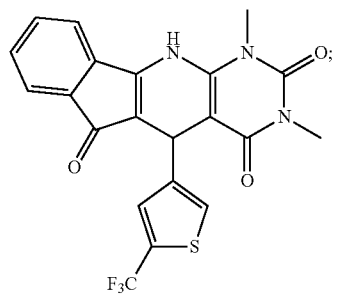 [SMILES: Cn1c2c(c(=O)n(C)c1=O)C(c1csc(C(F)(F)F)c1)C1=C(N2)c2ccccc2C1=O]

Compound II: 5-(4-trifluoromethylthiophen)-1,3-dimethyl-5,11-dihydro-1H-indeno-[2',1':5,6]pyrido[2,3-d]pyrimidine-2-thioxo-4,6-dione, which Chemical Structure is:

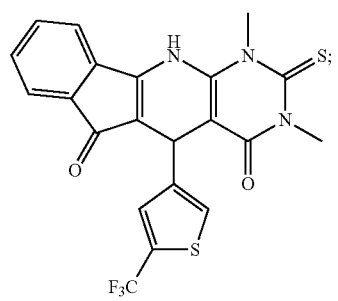 [SMILES: Cn1c2c(c(=O)n(C)c1=S)C(c1csc(C(F)(F)F)c1)C1=C(N2)c2ccccc2C1=O]

Compound III: 5-(3-fluoro-5-trifluoromethylphenyl)-1,3-dimethyl-5,11-dihydro-1H-indeno-[2',1':5,6]pyrido[2,3-d]pyrimidine-2-thioxo-4,6-dione, which Chemical Structure is:

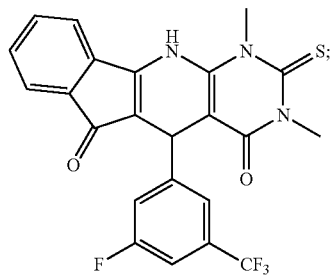 [SMILES: Cn1c2c(c(=O)n(C)c1=S)C(c1cc(F)cc(C(F)(F)F)c1)C1=C(N2)c2ccccc2C1=O]

Compound IV: 5-(3-fluoro-5-trifluoromethylphenyl)-1-ethyl-3-methyl-5,11-dihydro-1H-indeno-[2',1':5,6]pyrido[2,3-d]pyrimidine-2,4,6-trione

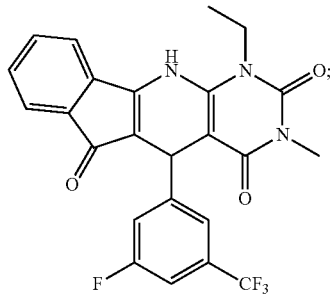 [SMILES: CCn1c2c(c(=O)n(C)c1=O)C(c1cc(F)cc(C(F)(F)F)c1)C1=C(N2)c2ccccc2C1=O]

Compound V: 5-(3,5-bistrifluoromethylphenyl)-1,3-dimethyl-5,11-dihydro-1H-indeno-[2',1':5,6]pyrido[2,3-d]pyrimidine-2-thioxo-4,6-dione, which Chemical Structure is:

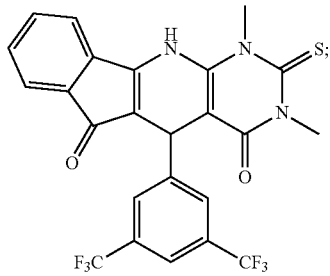 [SMILES: Cn1c2c(c(=O)n(C)c1=S)C(c1cc(C(F)(F)F)cc(C(F)(F)F)c1)C1=C(N2)c2ccccc2C1=O]

Compound VI: 5-(3,5-bistrifluoromethylphenyl)-1-ethyl-3-methyl-5,11-dihydro-1H-indeno-[2',1':5,6]pyrido[2,3-d]pyrimidine-2,4,6-trione, which Chemical Structure is:

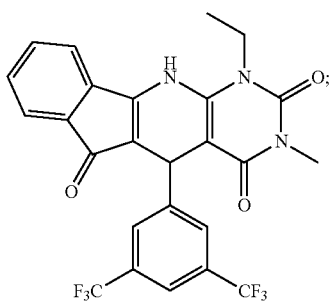 [SMILES: CCn1c2c(c(=O)n(C)c1=O)C(c1cc(C(F)(F)F)cc(C(F)(F)F)c1)C1=C(N2)c2ccccc2C1=O]

Compound VII: 5-(1,3-benzodioxol-4-yl)-1,3-dimethyl-5,11-dihydro-1H-indeno-[2',1':5,6]pyrido[2,3-d]pyrimidine-2,4,6-trione, which Chemical Structure is:

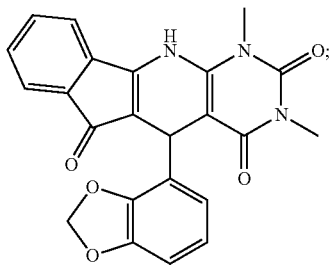 [SMILES: Cn1c2c(c(=O)n(C)c1=O)C(c1cccc3c1OCO3)C1=C(N2)c2ccccc2C1=O]

Compound VIII: 5-(1,3-benzodioxol-4-yl)-1,3-dimethyl-5,11-dihydro-1H-indeno-[2',1':5,6]pyrido[2,3-d]pyrimidine-2-thioxo-4,6-dione, which Chemical Structure is:

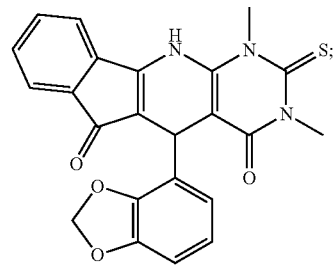 [SMILES: Cn1c2c(c(=O)n(C)c1=S)C(c1cccc3c1OCO3)C1=C(N2)c2ccccc2C1=O]

Compound IX: 5-(1,3-benzodioxol-5-yl)-1,3-dimethyl-5,11-dihydro-1H-indeno-[2',1':5,6]pyrido[2,3-d]pyrimidine-2,4,6-trione, which Chemical Structure is:

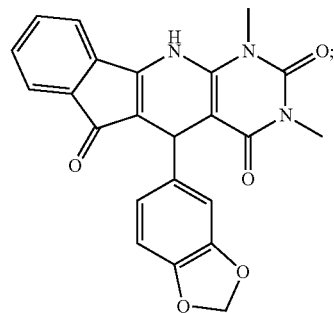 [SMILES: Cn1c2c(c(=O)n(C)c1=O)C(c1ccc3c(c1)OCO3)C1=C(N2)c2ccccc2C1=O]

Compound X: 5-(2,1,3-benzothiadiazol-4-yl)-1,3-dimethyl-5,11-dihydro-1H-indeno-[2',1':5,6]pyrido[2,3-d]pyrimidine-2,4,6-trione, which Chemical Structure is:

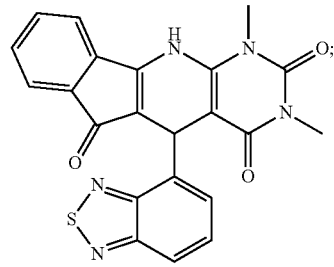 [SMILES: Cn1c2c(c(=O)n(C)c1=O)C(c1cccc3nsnc13)C1=C(N2)c2ccccc2C1=O]

Compound XI: 5-(2,1,3-benzothiadiazol-5-yl)-1,3-dimethyl-5,11-dihydro-1H-indeno-[2',1':5,6]pyrido[2,3-d]pyrimidine-2,4,6-trione, which Chemical Structure is:

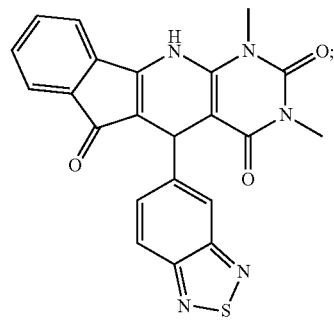 [SMILES: Cn1c2c(c(=O)n(C)c1=O)C(c1ccc3nsnc3c1)C1=C(N2)c2ccccc2C1=O]

Compound XII: 5-(2,1,3-benzothiadiazol-5-yl)-1,3-dimethyl-5,11-dihydro-1H-indeno-[2',1':5,6]pyrido[2,3-d]pyrimidine-2-thioxo-4,6-dione, which Chemical Structure is:

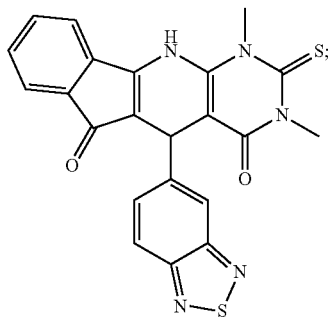 [SMILES: Cn1c2c(c(=O)n(C)c1=S)C(c1ccc3nsnc3c1)C1=C(N2)c2ccccc2C1=O]

and pharmaceutically acceptable salts thereof.

The new pyridopyrimidine derivative compounds can form pharmaceutically acceptable salts which are also within the scope of the present invention.

Examples of pharmaceutically acceptable salts of the General Formula (I) compound of the present invention are salts with mineral acids such as hydrochloric acid, sulfuric acid, nitric acid, phosphoric acid, hydrofluoric acid, hydrobromic acid, and the like, salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, and the like, and salts with alkali metal or alkali earth metals such as sodium, potassium, calcium, and the like.

The new pyridopyrimidine derivatives compounds, according to the invention, can be prepared by the following General Synthetic Route.

General Synthetic Route

Materials and Methods 5-(trifluoromethyl)thiophene-3-carbaldehyde was purchased from Aurora Building Blocks, 1-ethyl-3-methylurea was purchased from AKos Building Blocks and all the other commercial products have been purchased from Sigma Aldrich. All the reactions have been followed by TLC (Thin Layer Chromatography), carried out on Merck silica gel 60 F254 plates with fluorescent indicator and the plates have been visualized with UV light (254 nm). Preparative chromatographic purifications have been performed using silica gel column (Kieselgel 60). Solutions have been concentrated with a Büchi rotary evaporator at low pressure. Melting points, determined using a Büchi Melting Point B-540 instrument, are uncorrected and represent values obtained on recrystallized or chromatographically purified material. Molecular weights of intermediates and final compounds have been assessed by electrospray ionization mass spectrometry (ESI/MS) performed on an API 2000 Applied Biosystems mass spectrometer. The $^1$H-NMR spectra have been recorded on a Varian Mercury Plus 400 MHz instrument. All spectra have been recorded in DMSO-d6. The following abbreviations are used to describe peak patterns when appropriate: s (singlet), bs (broad singlet), d (doublet), dd (double doublet), t (triplet), q (quartet), m (multiplet).

General Procedure

The synthetic general procedure is based on the HANTZSCH and AGARWAL, dihydropyridine three component cyclization [A. HANTZSCH, "Condensationsprodukte aus Aldehydammoniak and ketonartigen Verbindungen". Chem. Ber., 1881, 14:1637-1638] and [A. AGARWAL et al., "First Report on the abnormal dearylation/alkylation reaction in one-pot hantzch synthesis with 6-Amino-1,3-Dimethyl Uracil". Synthetic Communications, 2004, 34:4447-4461]. In particular, reaction of the primary amines (c), synthesized when not commercially available (Synthetic procedures described in the Examples) with aldehydes (b), synthesized when not commercially available, and 1,3-indandione (a) in acetic acid afforded the desired compounds of General Formula (I).

The new pyridopyrimidine derivative compounds of General Formula (I) have been synthesized following the general synthetic route described in General Scheme below.

General Scheme

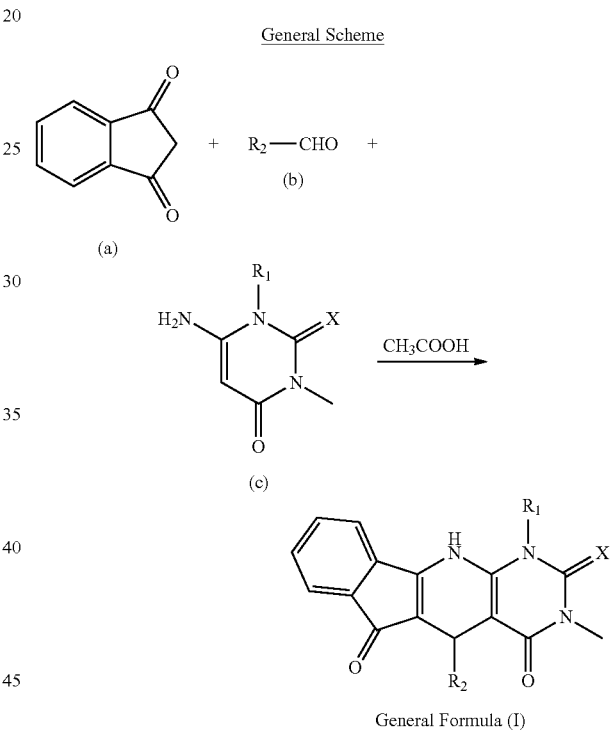

General Formula (I)

The following Examples describe the present invention in more details. It should be noted that the invention is not limited by the following Examples.

EXAMPLE 1

Preparation of Compound I

Synthesis of 5-(trifluoromethyl)thiophene-3-carbaldehyde

The compound 5-(trifluoromethyl)thiophene-3-carbaldehyde was obtained following a previously published procedure by BINDER [D. BINDER et al., "Thiophen als Strukturelement physiologisch aktiver Substanzen". Arch. Pharm. (Weinheim), 1985, 318:243-249]. 20 mL of a 20% solution of DIBAL in n-hexane were added dropwise during 30 min at a temperature below -45° C. under $N_2$ atmosphere to a solution of 3.1 g (17.5 mmol) of 5-(trifluoromethyl)thiophene-3-carbonitrile in 32.0 mL of anhydrous ether. The mixture was then stirred for 45 min at −30° C. and successively a 5% $H_2SO_4$ solution (3.0 mL) was added three times and the aqueous phase was extracted with diethyl ether. The combined organic phases were dried over $MgSO_4$. Solvent was evaporated to obtain desired compound as oil without further purification, and presented ESI-MS ($M_w$ 179.99): 180.8 (M+H$^+$). $^1$H-NMR (DMSO-d6): δ 9.95 (s, 1H), 8.35 (s, 1H), 7.95 (s, 1H).

Synthesis of Compound I

To acetic acid (15 mL) in a round bottom flask, (a) 1,3-indandione (0, 56 g, 3,83 mmol), (b) 5-(trifluoromethyl)thiophene-3-carbalbehyde (0.697 g, 3.93 mmol), and (c) 6-amino-1,3-dimethyluracil (0.5 g, 3.22 mmol) were added. The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound I.

m.p.: 265° C.

ESI-MS ($M_w$ 445.07): 445.9 (M+H$^+$).

$^1$H-NMR (DMSO-d6): δ 9.87 (s, 1H, NH), 7.87 (d, 1H), 7.63 (s, 1H), 7.59 (d, 1H), 7.48 (t, 1H), 7.36 (m, 2H), 4.88 (s, 1H), 3.55 (s, 3H), 3.13 (s, 3H).

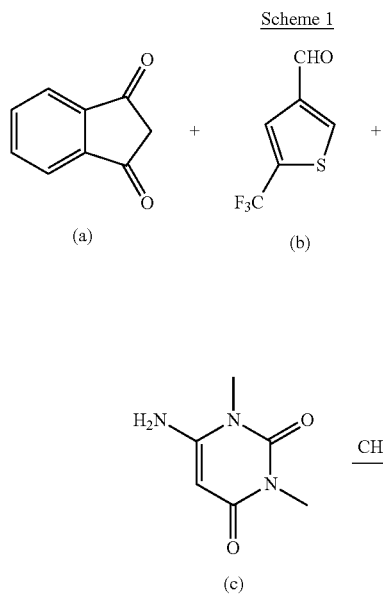

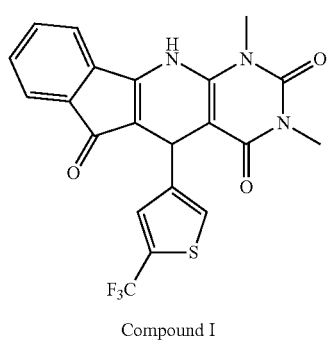

Compound I

EXAMPLE 2

Preparation of Compound II

Synthesis of 6-amino-1,3-dimethyl-2-thioxo-2,3-dihydropyrimidin-4(1H)-one.

The compound 6-amino-1,3-dimethyl-2-thioxo-2,3-dihydropyrimidin-4(1H)-one was obtained following a previously published procedure by HU [S. HU et al., "*Design, Synthesis and inhibitory activities of 8-(Substituted styrolformamido)phenyl-xanthine derivatives on monoamine oxidase B*". Chem. Pharm. Bull., 2012, 60(3):385-390], opportunely modified.

To a stirred solution of 1,3-dimethylthiourea (1.83 g, 17.57 mmol) in acetic anhydride (30 mL) was added cyanoacetic acid (1.5 g, 1.76 mmol), and the resulting mixture was stirred overnight at 70° C. The reaction mixture was concentrated and the resulting oily residue was diluted with $H_2O$ (40 mL) and treated with 5N NaOH (15 mL). The precipitate thus formed was collected by filtration, washed with cold water and purified by recrystallization from MeOH/$H_2O$ to give 6-amino-1,3-dimethyl-2-thioxo-2,3-dihydropyrimidin-4(1H)-one.

m.p. 289° C.

ESI-MS ($M_w$ 171.05): 172.1 (M+H$^+$).

$^1$H-NMR (DMSO-d6): δ 7.01 (s, 2H, $NH_2$), 5.01 (s, 1H), 3.74 (s, 3H), 3.50 (s, 3H).

Synthesis of Compound II

The Compound II was obtained with the same procedure described for Compound I in Example 1, by reaction of (a) 1,3-indandione (170 mg, 1,16 mmol), (b) 5-(trifluoromethyl)thiophene-3-carbalbehyde (209 mg, 1.18 mmol) and (c) 6-amino-1,3-dimethyl-2-thioxo-2,3-dihydropyrimidin-4(1H)-one (166 mg, 0.97 mmol). The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound II.

m.p.: 178° C.

ESI-MS ($M_w$ 461.05): 461.9 (M+H$^+$); 483.9 (M+Na$^+$).

$^1$H-NMR (DMSO-d6): δ 10.09 (s, 1H, NH), 7.87 (bs, 1H), 7.66 (bs, 1H), 7.60 (s, 1H), 7.49 (bs, 1H), 7.37 (m, 2H), 4.96 (s, 1H), 4.07 (s, 3H), 3.58 (s, 3H).

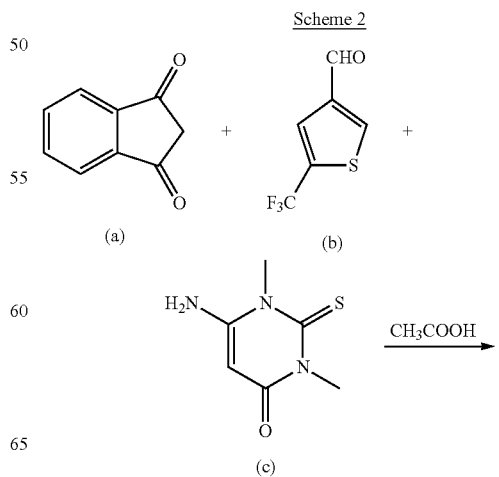

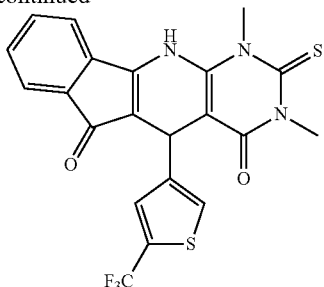

Compound II

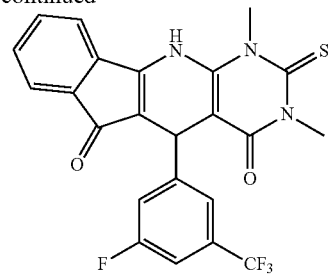

Compound III

EXAMPLE 3

Preparation of Compound III

Synthesis of Compound III

The Compound III was obtained with the same procedure described for Compound I in Example 1, by reaction of (a) 1,3-indandione (1.11 g, 7.57 mmol), (b) 3-fluoro-5-trifluoromethylbenzaldehyde (1.46 g, mmol 7.60) and (c) 6-amino-1,3-dimethyl-2-thioxo-2,3-dihydropyrimidin-4(1H)-one (1.08 g, 6.30 mmol). The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound III.

m.p.: 313° C.

ESI-MS (Mw 473.08): 474.1 (M+H+); 496.0 (M+Na+).

$^1$H-NMR (DMSO-d6): δ 10.12 (s, 1H, NH), 8.05 (d, 1H), 7.66 (s, 1H), 7.56 (s, 1H), 7.51 (d, 1H), 7.43 (t, 1H), 7.35 (t, 1H), 7.28 (s, 1H), 4.96 (s, 1H), 4.08 (s, 3H), 3.53 (s, 3H).

Scheme 3

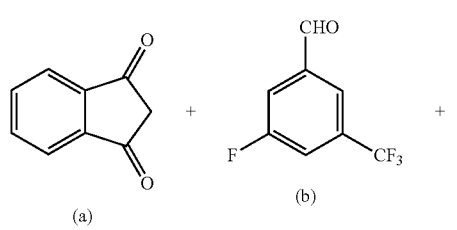

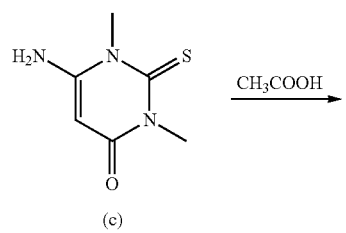

EXAMPLE 4

Preparation of Compound IV

Synthesis of 6-amino-1-ethyl-3-methylpyrimidine-2,4(1H,3H)-dione

The compound 6-amino-1-ethyl-3-methylpyrimidine-2,4 (1H,3H)-dione was obtained following a previously published procedure by HU [S. HU et al., "*Design, Synthesis and inhibitory activities of 8-(Substituted styrol-formamido) phenyl-xanthine derivatives on monoamine oxidase B*". Chem. Pharm. Bull., 2012, 60(3):385-390], opportunely modified.

To a stirred solution of 1-ethyl-3-methylurea (1.36 g, 13.3 mmol) in acetic anhydride (30 mL) was added cyanoacetic acid (1.13 g, 1.33 mmol) and the resulting mixture was stirred overnight at 70° C. The reaction mixture was concentrated and the resulting oily residue was diluted with $H_2O$ (40 mL) and treated with 5N NaOH (15 mL). The precipitate thus formed was collected by filtration, washed with cold water and purified by recrystallization from MeOH/$H_2O$ to give 1.91 g of 6-amino-1-ethyl-3-methylpyrimidine-2,4(1H,3H)-dione.

m.p. 232° C.

ESI-MS ($M_w$ 169.09): 170.1 (M+H$^+$).

$^1$H-NMR (DMSO-d6): δ 6.76 (s, 2H, NH$_2$), 4.64 (s, 1H), 3.80 (q, 2H), 3.29 (s, 3H), 1.08 (t, 3H).

Synthesis of Compound IV

The Compound IV was obtained with the same procedure described for Compound I in Example 1, by reaction of (a) 1,3-indandione (970 mg, 6.64 mmol), (b) 3-fluoro-5-trifluoromethylbenzaldehyde (1.27 g, 6.61 mmol) and (c) 6-amino-1-ethyl-3-methylpyrimidine-2,4(1H,3H)-dione (936 mg, 5,53 mmol). The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound IV.

m.p. 177° C.

ESI-MS ($M_w$ 471.12): 471.9 (M+H$^+$); 498.8 (M+Na$^+$).

$^1$H-NMR (DMSO-d6): δ 9.81 (s, 1H, NH), 7.94 (d, 1H), 7.49 (m, 3H), 7.40 (d, 1H), 7.33 (t, 1H), 7.27 (t, 1H), 4.91 (s, 1H), 4.26 (m, 2H), 3.10 (s, 3H), 1.24 (t, 3H).

Scheme 4

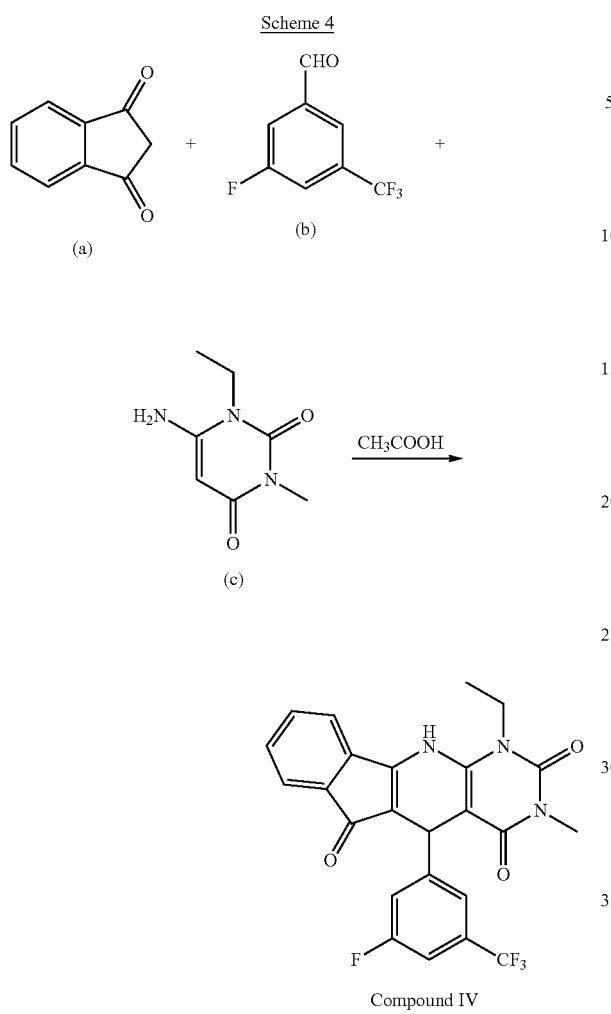

Scheme 5

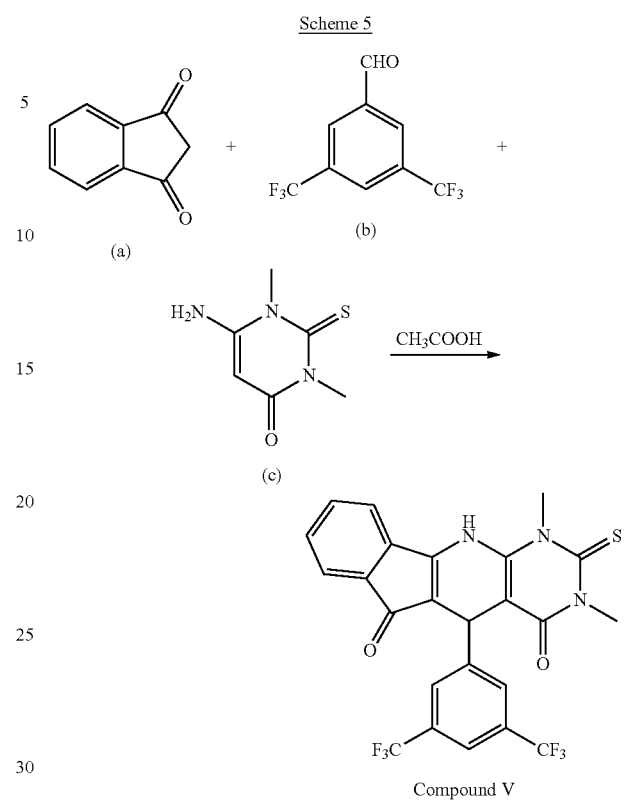

Compound V

EXAMPLE 5

Preparation of Compound V

Synthesis of Compound V

The Compound V was obtained with the same procedure described for Compound I in Example 1, by reaction of (a) 1,3-indandione (503 mg, 3.44 mmol), (b) 3,5-bistrifluoromethylbenzaldehyde (833 mg, 3.44 mmol) and (c) 6-amino-1,3-dimethyl-2-thioxo-2,3-dihydropyrimidin-4(1H)-one (490 mg, 2.86 mmol). The mixture was heated at reflux under nitrogen atmosphere for 8 h. It was then cooled to 0° C. The resulting precipitate was filtered and rinsed with cold water to obtain the crude product. Purification on silica gel column (CH$_2$Cl$_2$/CH$_3$OH, 9,5/0,5, v/v) afforded the desired Compound V.

m.p. 314° C.

ESI-MS (M$_w$ 523.08): 524.0 (M+H$^+$); 546.1 (M+Na$^+$).

$^1$H-NMR (DMSO-d6): δ 10.14 (s, 1H, NH), 8.08 (d, 1H), 7.97 (s, 2H), 7.87 (s, 1H), 7.53 (t, 1H), 7.37 (t, 1H), 7.27 (d, 1H), 5.06 (s, 1H), 4.08 (s, 3H), 3.51 (s, 3H).

EXAMPLE 6

Preparation of Compound VI

Synthesis of Compound VI

The Compound VI was obtained with the same procedure described for Compound I in Example 1, by reaction of (a) 1,3-indandione (708 mg, 4.84 mmol), (b) 3,5-bistrifluoromethylbenzaldehyde (1.17g, 4.83 mmol) and (c) 6-amino-1-ethyl-3-methylpyrimidine-2,4(1H,3H)-dione (683 mg, 4.04 mmol). The mixture was heated at reflux under nitrogen atmosphere for 8 h. It was then cooled to 0° C. The resulting precipitate was filtered and rinsed with cold water to obtain the crude product. Purification on silica gel column (CH$_2$Cl$_2$/CH$_3$OH, 9,5/0,5, v/v) afforded the desired Compound VI.

m.p. 166° C.

ESI-MS (M$_w$ 521.12): 522.1 (M+H$^+$).

$^1$H-NMR (DMSO-d6): δ 9.87 (s, 1H, NH), 7.94 (bs, 3H), 7.88 (s, 1H), 7.50 (t, 1H), 7.37 (t, 1H), 7.30 (d, 1H), 5.03 (s, 1H), 4.32 (m, 2H), 3.09 (s, 3H), 1.24 (t, 3H).

Scheme 6

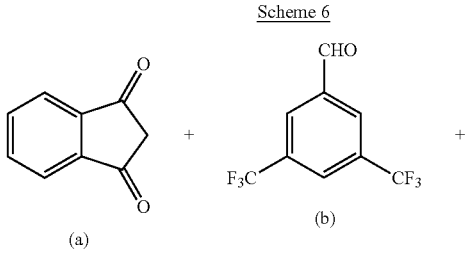

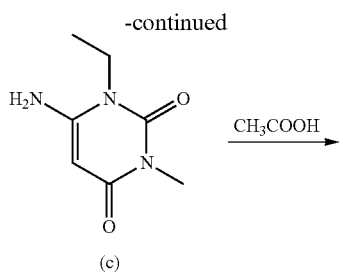

(c)

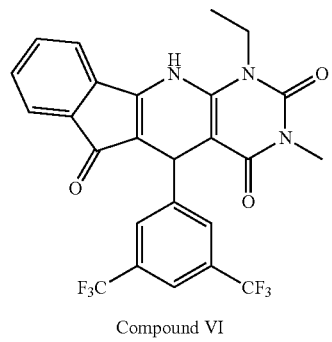

Compound VI

EXAMPLE 7

Preparation of Compound VII

Synthesis of 2,3-methylenedioxy)benzaldehyde

The compound 2,3-methylenedioxy)benzaldehyde was obtained following a previously published procedure by DEVEAU [A. M. DEVEAU, T. L. MACDONALD, "*Practical synthesis of biaryl colchicinoids containing 3',4'-catechol ether-based A-rings via Suzuki cross-coupling with ligandless palladium in water*". Tetrahedron Letters, 2004, 45:803-807].

To a flame-dried bottom flask equipped with a reflux condenser, 2,3-dihydroxybenzaldehyde (1 g; 7.24 mmol), DMF (dry, 30 mL) and cesium carbonate (1.5 eq) were sequentially added. After thorough mixing, dibromomethane (1.5 eq) was added via syringe. The mixture was heated at 110° C. for 2 hours, then cooled to room temperature. After filtering through a pad of celite, the filter cake was rinsed with EtOAc. The resultant organic filtrate was concentrated, diluted with water, and extracted three times with EtOAc. The combined organic phases were washed with water, dried over MgSO$_4$ and concentrated, in order to obtain a good yield of crude oil. Purification of the crude yellow oil by flash chromatography and kugelrohr distillation afforded the desired aldehyde which formed colorless translucent crystals upon cooling.

m.p. 35° C.

ESI-MS (M$_w$ 150.03): 151.1 (M+H$^+$).

$^1$H-NMR (DMSO-d6): δ 10.35 (s, 1H), 7.51 (dd, 1H), 7.24 (dd, 1H), 7.16 (dd,1H), 6.36 (s, 2H).

Synthesis of Compound VII

The Compound VII was obtained with the same procedure described for Compound I in Example 1, by reaction of (a) 1,3-indandione (1.61 g, 11.02 mmol), (b) 2,3-(methylenedioxy)benzaldehyde (1.66g, 11.06 mmol) and (c) 6-amino-1,3-dimethyluracil (1,43 g, 9.22 mmol). The mixture was heated at reflux under nitrogen atmosphere for 8 h. It was then cooled to 0° C. The resulting precipitate was filtered and rinsed with cold water to obtain the crude product. Purification on silica gel column (CH$_2$Cl$_2$/CH$_3$OH, 9,5/0,5, v/v) afforded the desired Compound VII.

m.p. 300° C.

ESI-MS (M$_w$ 415.12): 416.0 (M+H$^+$); 438.0 (M+Na$^+$).

$^1$H-NMR (DMSO-d6): δ 9.88 (s, 1H, NH), 7.83 (d, 1H), 7.45 (t, 1H), 7.32 (t, 1H), 7.24 (d, 1H), 6.73 (t, 1H), 6.66 (d, 2H), 5.90 (d, 2H), 4.81 (s, 1H), 3.56 (s, 3H), 3.08 (s, 3H).

Scheme 7

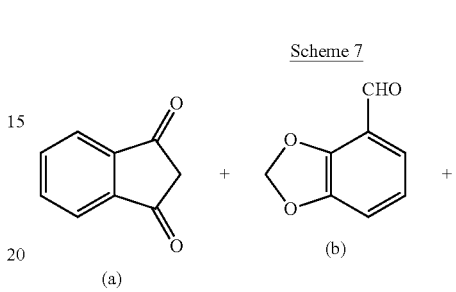

Compound VII

EXAMPLE 8

Preparation of Compound VIII

Synthesis of Compound VIII

The Compound VIII was obtained with the same procedure described for Compound I, by reaction of (a) 1,3-indandione (535 mg, 3.66 mmol), (b) 2,3-(methylenedioxy)benzaldehyde (549 mg, 3.66 mmol) and (c) 6-amino-1,3-dimethyl-2-thioxo-2,3-dihydropyrimidin-4(1H)-one (521 mg, 3.05 mmol). The mixture was heated at reflux under nitrogen atmosphere for 8 h. It was then cooled to 0° C. The resulting precipitate was filtered and rinsed with cold water to obtain the crude product. Purification on silica gel column (CH$_2$Cl$_2$/CH$_3$OH, 9,5/0,5, v/v) afforded the desired Compound VIII.

m. p. 310° C.

ESI-MS (M$_w$ 431.09): 432.0 (M+H$^+$); 453.9 (M+Na$^+$).

$^1$H-NMR (DMSO-d6): δ 10.11 (s, 1H, NH), 7.83 (d, 1H), 7.47 (t, 1H), 7.34 (t, 1H), 7.27 (d, 1H), 6.77 (bs, 1H), 6.68 (bs, 2H), 5.93 (d, 2H), 4.88 (s, 1H), 4.08 (s, 3H), 3.53 (s, 3H).

Scheme 8

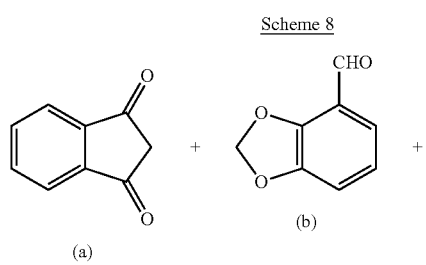

Compound VIII

EXAMPLE 9

Preparation of Compound IX

Synthesis of 3,4-(methylenedioxy)benzaldehyde

The compound 3,4-(methylenedioxy)benzaldehyde was obtained following a previously published procedure by POLI [G. POLI, G. GIANBASTIANI, "*An Epiisopicropodophyllin aza analogue via Palladium-catalyzed pseudo-domino cyclization*". *J. Org. Chem.*, 2002, 67:9456-9459].

To a solution of piperonyl alcohol (10 g, 65.73 mmol) in $CH_2Cl_2$ (250 mL), $MnO_2$ (49.3 g, 567.32 mmol) was added in one portion. The resulting dark suspension was stirred at room temperature for 24 h, and then filtered off throw a celite pad washing with $CH_2Cl_2$. The solvent was removed in vacuum and the resulting crude crystalline yellow pale solid was used without further purification.

m.p. 338° C.

ESI-MS ($M_w$ 150.03): 151.1 (M+H$^+$).

$^1$H-NMR (DMSO-d6): δ 9.80 (s, 1H), 7.40 (m, 2H), 6.92 (d, 1H), 6.07 (s, 2H).

Synthesis of Compound IX

The Compound IX was obtained with the same procedure described for compound I in Example 1, by reaction of (a) 1,3-indandione (203 mg, 1.39 mmol), (b) 3,4-(methylenedioxy)benzaldehyde (209 mg, 1.39 mmol) and (c) 6-amino-1,3-dimethyluracil (180 mg, 1.16 mmol). The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound IX.

m.p. 338° C.

ESI-MS ($M_w$ 415.12): 416.0 (M+H$^+$); 437.9 (M+Na$^+$); 453.9 (M+K$^+$).

$^1$H-NMR (DMSO-d6): δ 9.79 (s, 1H, NH), 7.98 (d, 1H), 7.46 (t, 1H), 7.33 (t, 1H), 7.27 (d, 1H), 6.81 (s, 1H), 6.72 (bs, 2H), 5.89 (s, 2H), 4.69 (s, 1H), 3.57 (s, 3H), 3.10 (s, 3H).

Scheme 9

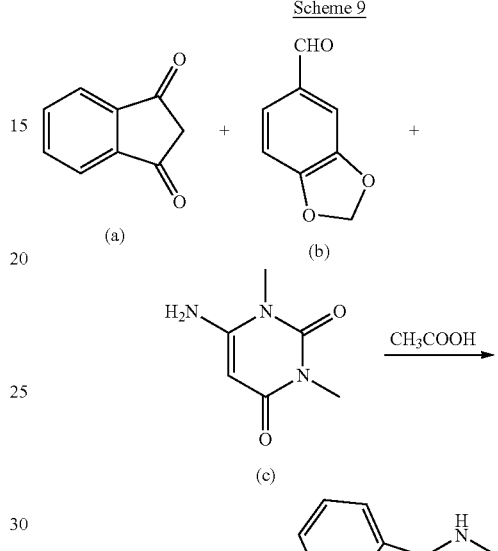

Compound IX

EXAMPLE 10

Preparation of Compound X

Synthesis of 2,1,3-benzothiadiazol-4-carboxaldehyde

The compound 2,1,3-benzothiadiazol-4-carboxaldehyde was obtained following a previously published procedure by VANELLE [P. VANELLE, C. T. LIEGEOIS, J. MEUCHE, J. MALDONADO, M. P. CROZET, "*An original way for synthesis of new nitrobenzothiadiazole derivatives*". *Heterocycles*, 1997, 45(5):955-962].

The lithium salt of 2-nitropropane (2.48 g, 27.84 mmol) was added to a solution of 4-bromomethyl-2,1,3-benzothiadiazole (5.82 g, 25.40 mmol) in methanol (60 mL). After stirring at room temperature (approximately 25° C.) for 24 h, methanol was distilled off on a rotatory evaporator under reduced pressure. The residue was dissolved in dichloromethane and the solvent was washed with water, dried over anhydrous magnesium sulfate and evaporated under vacuum. After purification by recrystallization from cyclohexane, 2,1,3-benzothiadiazol-4-carboxaldehyde was obtained as a yellow solid.

m.p. 99° C.

ESI-MS ($M_w$ 164.18): 165.2 (M+H$^+$).

$^1$H-NMR (DMSO-d6): δ 10.60 (s, 1H), 8.43 (d, 1H), 8.27 (d, 1H), 7.91 (t, 1H).

Synthesis of Compound X

The Compound X was obtained with the same procedure described for Compound I in Example 1, by reaction of (a) 1,3 indandione (420 mg, 2.87 mmol), (b) 2,1,3-benzothiadiazol-4-carboxaldehyde (471 mg, 2.87 mmol) and (c) 6-amino-1,3-dimethyluracil (359 mg, 2.31 mmol). The mixture was heated at reflux under nitrogen atmosphere for 8 h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound X.

m.p. 331° C.

ESI-MS ($M_w$ 429.09): 430.1 (M+H$^+$); 452.0 (M+Na$^+$); 467.9 (M+K$^+$).

$^1$H-NMR (DMSO-d6): δ 10.08 (s, 1H, NH), 7.88 (d, 1H), 7.62 (d, 3H), 7.50 (t, 1H), 7.32 (t, 1H), 7.23 (d, 1H), 5.46 (s, 1H), 3.64 (s, 3H), 3.01 (s, 3H).

Scheme 10

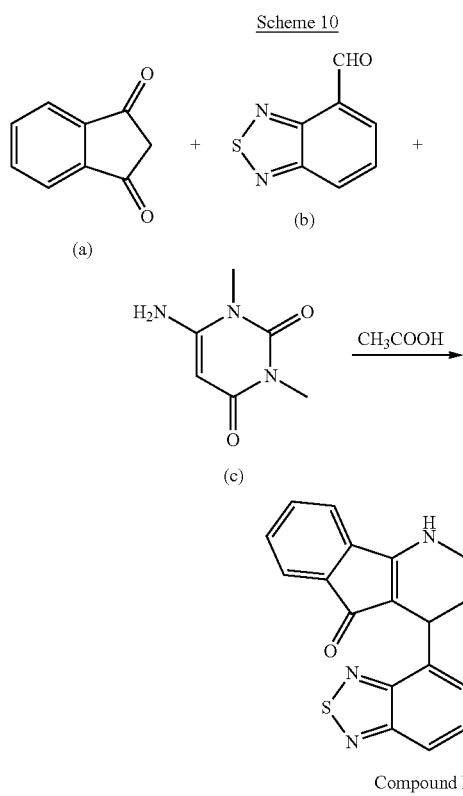

Compound X

EXAMPLE 11

Preparation of Compound XI

Synthesis of 2,1,3-benzothiadiazol-5-carboxaldehyde

The compound 2,1,3-benzothiadiazol-5-carboxaldehyde was obtained following a previously published procedure by CARROLL [W. A. CARROLL, et al., "*Synthesis and Structure—Activity relationships of a novel series of* 2,3,5,6,7,9-*Hexahydrothieno[3,2-b]quinolin-8(4H)-one 1,1-dioxide $K_{ATP}$ channel openers: Discovery of* (-)-(9S)-9-(3-*bromo-4-fluorophenyl*)-2,3,5,6,7,9-*hexahydrothieno[3,2-b]quinlin-8 (4H) -one 1,1-Dioxide (A-278637), a Potent $K_{ATP}$ Opener that selectively inhibits spontaneous bladder contractions*". J. Med. Chem., 2004, 47:3163-3179].

The 5-Hydroxy-methylbenzo-2,1,3-thiadiazole (2,6 g, 16 mmol) and $MnO_2$ (5.6 g, 64.41 mmol) in $CHCl_3$ (150 mL) were stirred at room temperature (approximately 25° C.) overnight. The reaction mixture was filtered and the filtrate evaporated. Crude residue was submitted to the chromatograph on silica gel (EtOAc/Hexane, 7/3, v/v) to provide 1.9 g of 2,1,3-benzothiadiazole-5-carboxaldehyde.

m.p. 93° C.

ESI-MS ($M_w$ 164.18): 165.2 (M+H$^+$).

$^1$H-NMR (DMSO-d6): 10.21 (s, 1H), 8.78 (d, 1H), 8.19 (d, 1H), 8.04 (s, 1H).

Synthesis of Compound XI

The Compound XI was obtained with the same procedure described for compound I in Example 1, by reaction of (a) 1,3-indandione (468 mg, 3.20 mmol), (b) 2,1,3-benzothiadiazol-5-carboxaldehyde (525 mg, 3.20 mmol) and (c) 6-amino-1,3-dimethyluracil (415 mg, 2.67 mmol). The mixture was heated at reflux under nitrogen atmosphere for 8h. It was then cooled to 0° C. The resulting precipitate was filtered and rinsed with cold water to obtain the crude product. Purification on silica gel column ($CH_2Cl_2/CH_3OH$, 9,5/0,5, v/v) afforded the desired Compound XI.

m.p. 358° C.

ESI-MS ($M_w$ 429.09): 430.1 (M+H$^+$); 452.1 (M+Na$^+$).

$^1$H-NMR (DMSO-d6): δ 9.92 (s, 1H, NH), 7.93 (m, 3H), 7.77 (d, 1H), 7.47 (t, 1H), 7.33 (t, 1H), 7.26 (d, 1H), 4.99 (s, 1H), 3.61 (s, 3H), 3.08 (s, 3H).

Scheme 11

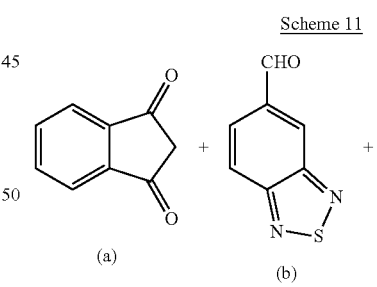

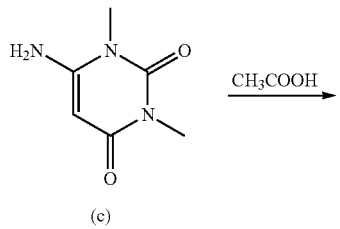

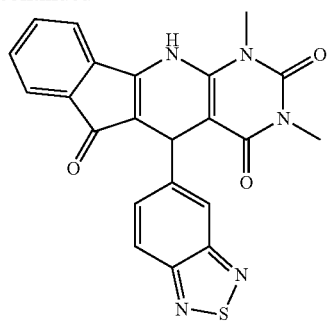

Compound XI

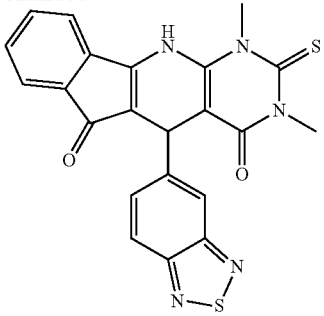

Compound XII

EXAMPLE 12

Preparation of Compound XII

Synthesis of Compound XII

The compound was obtained with the same procedure described for Compound I in Example 1, by reaction of (a) 1,3-indandione (456 mg, 3.12 mmol), (b) 2,1,3-benzothiadiazol-5-carboxaldehyde (512 mg, 3.12 mmol) and (c) 6-amino-1,3-dimethyl-2-thioxo-2,3-dihydropyrimidin-4 (1H)-one (445 mg, 2.60 mmol). The mixture was heated at reflux under nitrogen atmosphere for 8 h. It was then cooled to 0° C. The resulting precipitate was filtered and rinsed with cold water to obtain the crude product. Purification on silica gel column (CH$_2$Cl$_2$/CH$_3$OH, 9,5/0,5, v/v) afforded the desired Compound XII.

m.p. 362° C.

ESI-MS (M$_w$ 445.07): 446.0 (M+H$^+$); 468.0 (M+Na$^+$).

$^1$H-NMR (DMSO-d6): δ 10.14 (s, 1H, NH), 7.96 (m, 3H), 7.80 (d, 1H), 7.48 (t, 1H), 7.34 (t, 1H), 7.27 (d, 1H), 5.04 (s, 1H), 4.11 (s, 3H), 3.51 (s, 3H).

Scheme 12

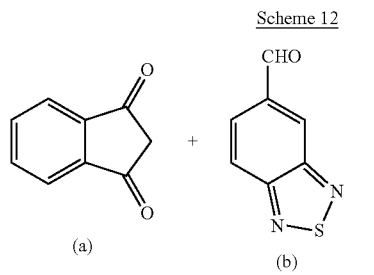

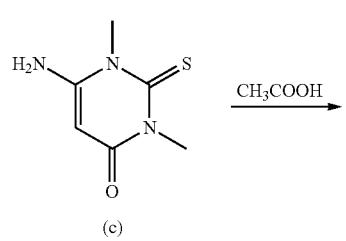

In some aspects, the present invention also provides a pharmaceutical composition, e.g. an appropriate dosage form, wherein said composition comprises as active ingredient an effective amount of one or more compounds with structure represented by General Formula (I), or pharmaceutically acceptable salts thereof, or their mixtures (in any ratio); and pharmaceutically acceptable excipients.

The pharmaceutical composition, according to present invention, is administered by any adequate route, for example, by oral, sublingual, rectal, vaginal, nasal, intraperitoneal or parenteral routes, but not limited of these examples. The preferred route is oral.

The pharmaceutical compositions for oral administration can be presented in diverse pharmaceutical forms, such as, but not limited to: (i) tablet, optionally coated, chewable, effervescent, multilayered or dispersible; (ii) pills; (iii) powder, optionally dispersible or effervescent; (iv) capsule, optionally hard gelatinous capsule, softgel or amylaceous gelatinous capsule; (v) lozenge; (vi) granule, optionally in the form of microparticles, microcapsules, or vectorized preparations, like, liposomes; (vii) suppositories; (viii) solution; (ix) syrup; (x) suspension; (xi) injectable; and others.

The pharmaceutical composition, according to present invention, is for use as inhibitor of the cyclic nucleotide synthesis. In another embodiment, the pharmaceutical composition is for use as inhibitor of the cAMP and cGMP synthesis.

The pharmaceutical composition, according to present invention, is used in the prophylactic and/or curative treatment of diarrhea, colitis and irritable bowel syndrome.

The pharmaceutical composition, according to present invention, may be prepared by methods well known in the state of the art. Appropriately, Remington's Pharmaceutical Sciences or similar information sources may be used to prepare a suitable formulation according to the invention.

Test Compounds

EXAMPLE 13

Protocol for the Stimulation of Guanylate Cyclase-C Induced by the Toxin STa in T84 Cells a) Cells Growing Cells from the T84 line (ATCC CCL-248) are subculture according to supplier's instructions. Briefly, after washing the culture flask (75 cm$^2$) using 3 mL of 0.25% Trypsin solution (w/v) and 0.53 mM EDTA solution to remove the traces of serum, the same volume of trypsin is added to each bottle, and cells are observed under a microscope until detachment of the cellular layer (usually 8-10 minutes).

Preparation of assay plates (12-well plates) follows after adding 8 mL of culture medium (DMEM-F12 supplemented with 10% fetal bovine serum and penicillin-streptomycin (50IU/mL:50pg/mL) and centrifugation of the cell homogenate at 2000 rpm for 5 minutes (at 25° C.).

With the aid of a 1 mL pipet connected to a vacuum pump, the supernatant is aspirated and the cells resuspended with culture medium (with necessary volume to maintain the ratio of 1:4, i.e. 1 culture flask originates 4 12-well plates). After homogenization of the cells, with an aid of a pipette, it is added 2 mL of the cell suspension to each well of the plate. The growth occurs in an incubator under controlled conditions (37° C., 5% $CO_2$ atmosphere) until confluence of each well (typically 8-10 days).

b) Method

Initially, the culture medium is aspirated using a 1 mL pipette connected to a vacuum pump and the cells are washed at least 3 times with 0.5 mL of a Dulbecco Phosphate Buffered Saline (DPBS; 37° C.) using a 1 mL pipette attached to one the vacuum pump. In the sequence, 0.5 mL of DPBS is added in the presence and/or absence of 1-metil-3-isobutyl xanthine (1 mM), dimethylsulfoxide (0.1% v/v) and the test compound and incubated for 10 minutes in an oven (37° C., 5% $CO_2$ atmosphere).

After the incubation period, the cells are stimulated with STa toxin (1 µM, 5 µL) and incubated in an incubator (37° C., 5% $CO_2$ atmosphere) for 10 minutes. After the stimulation period, the volume of the supernatant is aspirated using a 1 mL pipette connected to a vacuum pump and the cGMP is extracted by the addition of a hydrochloric acid solution 0.1 M (0.3 mL, using a pipette), pH 4, under constant stirring (speed 4) in a shaker type "rotator" (Lab-line Instruments, model number 4625), for 20 minutes. After the extraction period, the volume of each well is centrifuged (15000 rpm, 5 minutes, 25° C.) and an aliquot of the supernatant (0.3 mL) is quickly stored in a freezer at −20° C. for the subsequent quantification of the content of cGMP by the immunoassay method developed and described by HORTON et al. (1992) [Horton, J. K.; Martin, R. C.; Kalinka, S.; Cushing, A.; Kitcher, J. P.; O'Sullivan, M. J.; Baxendale, P. M., "*Enzime immunoassays for the estimation of adenosine 3',5' cyclic monophosphate and guanosine 3',5' cyclic monophosphate in biological fluids*". J Immunol Methods 1992, 155:31-40].

The protein precipitate or "pellets" are digested directly by the addition of 0.5 mL of a 0.1 M sodium hydroxide solution, under constant agitation in a shaker type "rotator" (speed 7), for 30 minutes. Posteriorly, this protein fraction is used in the tests to determine proteins, employing a method developed by BRADFORD (1976). M. M. BRADFORD, "*A rapid and sensitive method for the quantitation of microgram quantities of protein utilizing the principle of protein-dye binding*". Analytical Biochemistry, 1976, 72:248-254].

c) Compounds Tested

The compounds tested are I, II, III, IV, V, VI, VII, VIII, IX, X, XI, and XII; described in TABLE 1.

d) Results

TABLE 2

Effect of Compounds II, IV, VI, VIII and X on cGMP accumulation induced by STa (1 µM) in T84 cells (see FIG. 1)

| Compound(s) | cGMP, pmol/10 min/mg | % of inhibition (Compound × STa) |
|---|---|---|
| Baseline | 6.18 ± 0.49 | — |
| STa (1 µM) | 1044.0 ± 55.42[#] | — |
| FPIPP (50 µM) | 53.53 ± 6.22* | ~94 |

TABLE 2-continued

Effect of Compounds II, IV, VI, VIII and X on cGMP accumulation induced by STa (1 µM) in T84 cells (see FIG. 1)

| Compound(s) | cGMP, pmol/10 min/mg | % of inhibition (Compound × STa) |
|---|---|---|
| II (50 µM) | 57.50 ± 3.16* | ~94 |
| IV (50 µM) | 146.80 ± 22.94* | ~86 |
| VI (50 µM) | 22.83 ± 3.30* | ~97 |
| VIII (50 µM) | 350.70 ± 35.80* | ~66 |
| X (50 µM) | 668.40 ± 75.46* | ~36 |

Results are expressed as mean ± SEM.
[#]$p < 0.05$, compared with Baseline group;
*$p < 0.05$, compared with STa group; (ANOVA followed by Tukey's test).

TABLE 3

Figure 2:
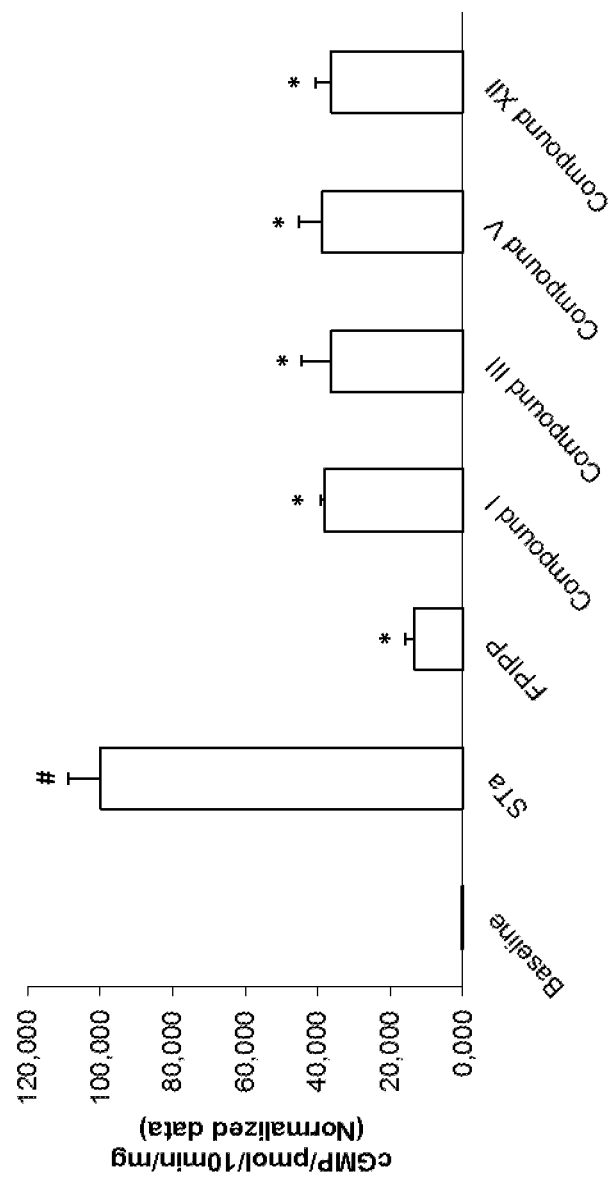
FIG. 2: Effect of Compounds I, III, V and XII on cGMP accumulation induced by STa (1 μM) in $T_{84}$ cells.

Effect of Compounds I, III, V and XII on cGMP accumulation induced by STa (1 µM) in T84 cells (see FIG. 2)

| Compound(s) | cGMP, pmol/10 min/mg | % of inhibition (Compound × STa) |
|---|---|---|
| Baseline | 0.02 ± 0.01 | — |
| STa (1 µM) | 554.20 ± 49.43[#] | — |
| FPIPP (50 µM) | 74.83 ± 13.26* | ~86 |
| I (50 µM) | 210.70 ± 6.11* | ~62 |
| III (50 µM) | 201.50 ± 44.93* | ~64 |
| V (50 µM) | 215.50 ± 34.57* | ~62 |
| XII (50 µM) | 201.50 ± 23.51* | ~64 |

Results are expressed as mean ± SEM.
[#]$p < 0.05$, compared with Baseline group;
*$p < 0.05$, compared with STa group; (ANOVA followed by Tukey's test).

TABLE 4

Figure 3:
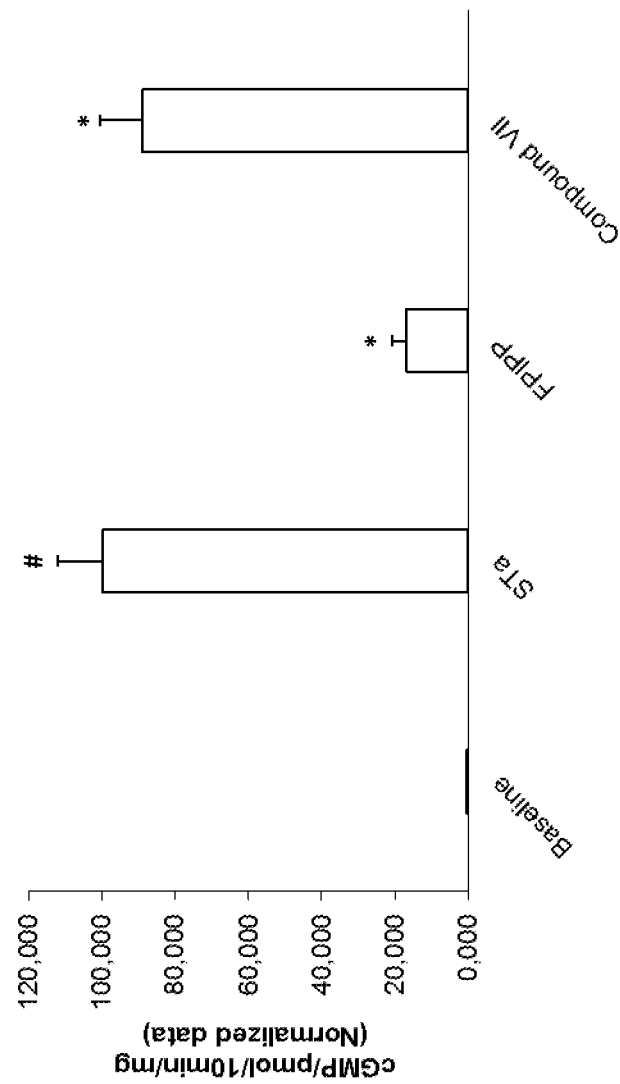
FIG. 3: Effect of Compound VII on cGMP accumulation induced by STa (1 μM) in $T_{84}$ cells.

Effect of compound VII on cGMP accumulation induced by STa (1 µM) in T84 cells (see FIG. 3)

| Compound(s) | cGMP, pmol/10 min/mg | % of inhibition (Compound × STa) |
|---|---|---|
| Baseline | 0.25 ± 0.06 | — |
| STa (1 µM) | 334.60 ± 40.74[#] | — |
| FPIPP (50 µM) | 56.25 ± 13.61* | ~83 |
| VII (50 µM) | 297.30 ± 39.06* | ~12 |

Results are expressed as mean ± SEM.
[#]$p < 0.05$, compared with Baseline group;
*$p < 0.05$, compared with STa group; (ANOVA followed by Tukey's test).

TABLE 5

Figure 4:
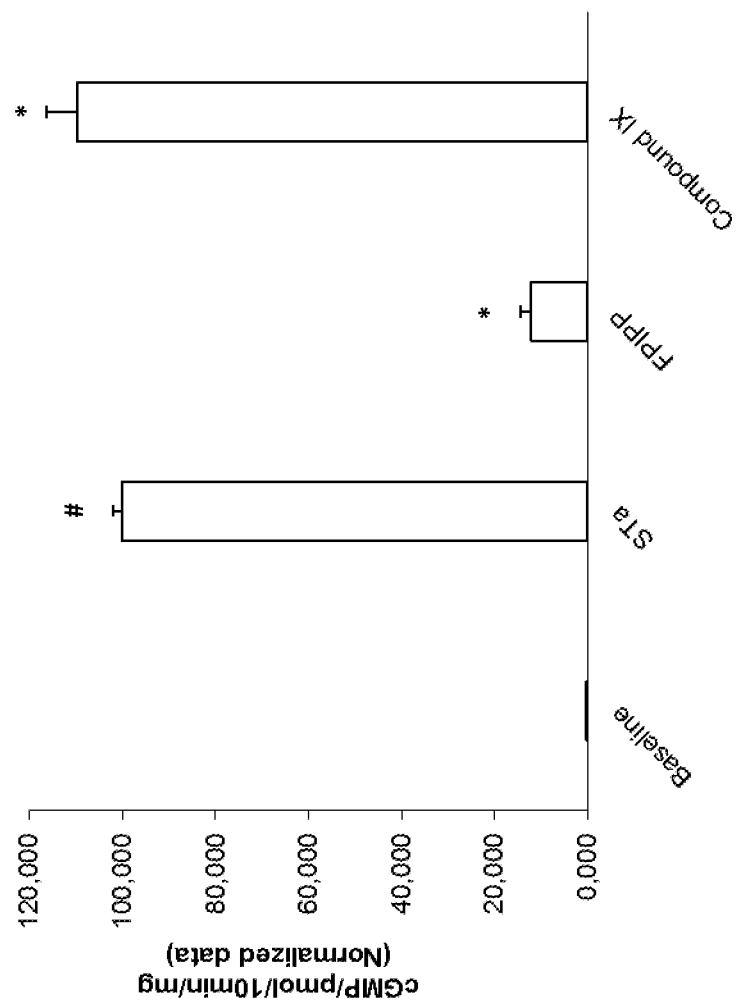
FIG. 4: Effect of Compound IX on cGMP accumulation induced by STa (1 μM) in $T_{84}$ cells.

Effect of compound IX on cGMP accumulation induced by STa (1 µM) in T84 cells (see FIG. 4)

| Compound(s) | cGMP, pmol/10 min/mg | % of inhibition (Compound × STa) |
|---|---|---|
| Baseline | 5.62 ± 0.59 | — |
| STa (1 µM) | 642.80 ± 11.60[#] | — |
| FPIPP (50 µM) | 81.00 ± 14.38* | ~87 |
| IX (50 µM) | 703.50 ± 43.11* | — |

Results are expressed as mean ± SEM.
[#]$p < 0.05$, compared with Baseline group;
*$p < 0.05$, compared with STa group; (ANOVA followed by Tukey's test).

TABLE 6

Figure 5:
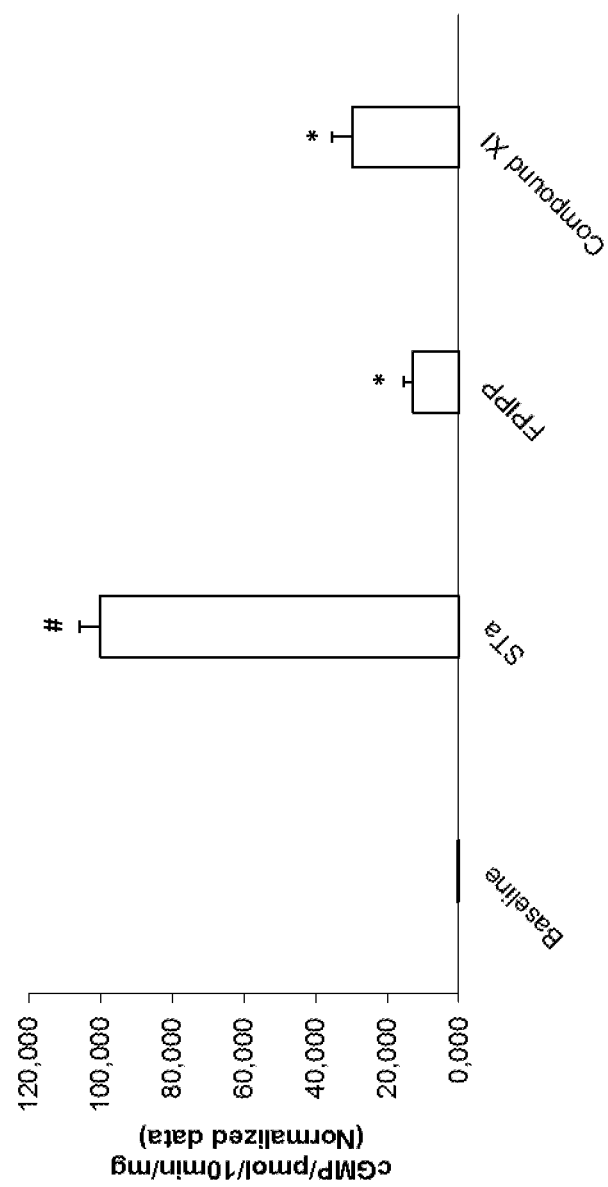
FIG. 5: Effect of Compound XI on cGMP accumulation induced by STa (1 μM) in $T_{84}$ cells.

Effect of compound XI on cGMP accumulation induced by STa (1 μM) in T84 cells (see FIG. 5)

| Compound(s) | cGMP, pmol/10 min/mg | % of inhibition (Compound × STa) |
|---|---|---|
| Baseline | 0.02 ± 0.01 | — |
| STa (1 μM) | 575.50 ± 33.01# | — |
| FPIPP (50 μM) | 74.83 ± 13.26* | ~86 |
| XI (50 μM) | 171.30 ± 31.68* | ~70 |

Results are expressed as mean ± SEM.
p < 0.05, compared with Baseline group;
*p < 0.05, compared with STa group; (ANOVA followed by Tukey's test).

EXAMPLE 14

Protocol for Determination of Absolute Bioavailability a) Animals

The study used male Beagle dogs, aged between 2 to 4 years old, weighing between 8 to 12 kg, and kept in food control and disposal of water ad libitum during the study.

b) Animal Preparation

The dogs were shaving in the radial portion of the front paws, performing aseptic on site with the aid of moistened gauze with 70% alcohol.

Entered the 21G catheter (one in each paw in the intravenous administration protocol and a single paw in the oral administration protocol) in order to access the cephalic vein.

The blood samples were collected from animals depending on the established sampling times by taking 1.5 mL of blood using a 3 mL syringe. The samples were transferred to heparinized tube collection.

c) Route of Administration

The administration of the study compounds was made orally and intravenously.

The intravenous administration of the compounds was carried out in bolus, and has through one of the cephalic veins of dogs. Concentrations were administered 1 mg/kg; 3 mg/kg and 10 mg/kg in one, on different days.

The oral administration of the drug was provided as a powder in capsules at the dose of 3 mg/kg, which were all completely ingested by dogs.

d) Sampling Times

For the intravenous administration, the blood samples (1.5 ml) were collected in the following predetermined time intervals: 0, 0.033, 0.083, 0.17, 0.25, 0.33, 0 5; 1; 2; 3; 4; 6; 8; 12 and 24 hours.

For the oral administration, the blood samples (1.5 ml) were collected in the following predetermined time intervals: 0, 0.33, 0.67, 1, 1.5, 2, 3, 4, and 6, 8, 12 and 24 hours.

e) Compounds Tested

The compounds tested are II, IV, VI, and XI; described in TABLE 1.

f) Analytical Method

The heparinized tubes collections were placed in a centrifuge and were processed for 10 minutes at 2500 rpm per minute. The plasma was separated and put into other tubes. The plasma was analyzed by Liquid chromatography-tandem mass spectrometry (LC-MS/MS).

g) Results

TABLE 7

Results obtained of the compounds II, IV, VI, and XI were:

| Compound(s) | Absolute bioavailability |
|---|---|
| II | 0.16% |
| IV | 0.17% |
| VI | 0.82% |
| XI | 0.35% |

All four compounds tested for inhibition of cyclic nucleotide showed negligible absolute bioavailability. These results indicate great therapeutic potential thereof for the treatment of disorders of the intestinal tract, since no absolute bioavailability greatly reduces the possibility of these compounds present some kind of systemic toxicity.

The compounds of the present invention, new pyridopyrimidine derivatives compounds, are useful in human and veterinary medicine for treating a condition in a patient. In accordance with the present invention, said compounds can be administered to a patient in need of prevention and/or treatment of a condition.

The present invention also describes a method for using the new pyridopyrimidine derivatives compounds as inhibitor of the cyclic nucleotide synthesis. In another embodiment, describes a method for using the new pyridopyrimidine derivatives compounds as inhibitor of the cAMP and cGMP synthesis.

Another objective of the present invention is the use of the new pyridopyrimidine derivatives compounds, their pharmaceutically acceptable salts or mixtures thereof (in any ratio), for inhibiting the cyclic nucleotide synthesis. Furthermore, it is the objective of the present invention the use of one of the new pyridopyrimidine derivatives compounds, their pharmaceutically acceptable salts or mixtures thereof (in any ratio), for inhibiting the cAMP and cGMP synthesis.

It is also the objective of the present invention the use of one of the new pyridopyrimidine derivatives compounds, their pharmaceutically acceptable salts or mixtures thereof (in any ratio), in the prophylactic and/or curative treatment of diarrhea, colitis and irritable bowel syndrome.

The invention claimed is:

1. A compound represented by General Formula (I):

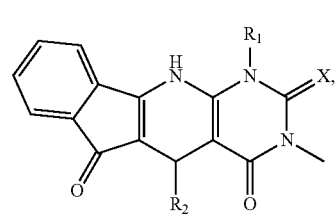

General Formula (I)

or a pharmaceutically acceptable salt thereof, or their mixtures in any ratio, wherein:

$R_1$ is ethyl;

$R_2$ is selected from the group consisting of 4-(trifluoromethyl)thiophene, 3-fluoro-5-trifluoromethylphenyl, 3,5-bistrifluoromethylphenyl, 1,3-benzodioxol-4-yl, 2,1,3-benzothiadiazol-4-yl, and 2,1,3-benzothiadiazol-5-yl; and X is O or S.

2. The compound according to claim 1 wherein it is:

(Compound IV)

3. The compound according to claim 1 wherein it is:

(Compound VI)

4. A pharmaceutical composition comprising as active ingredient an effective amount of one or more compounds according to claim 1, or pharmaceutically acceptable salts thereof; and pharmaceutically acceptable excipients.

5. The pharmaceutical composition according to claim 4, wherein said composition is for inhibition of the cyclic nucleotide synthesis.

6. The pharmaceutical composition according to claim 4, wherein said composition is for inhibition of the cAMP and cGMP synthesis.

7. The pharmaceutical composition according to claim 4, wherein said composition is for the treatment of diarrhea, colitis and irritable bowel syndrome.

8. A method of inhibiting the cyclic nucleotide synthesis in a patient, comprising administering the pharmaceutical composition according to claim 4 to said patient.

9. A method of inhibiting the cAMP and cGMP synthesis in a patient, comprising administering the pharmaceutical composition according to claim 4 to said patient.

10. A method for treatment of diarrhea, colitis and irritable bowel syndrome in a patient in need thereof, comprising administering the pharmaceutical composition according to claim 4 to said patient.

11. A method of inhibiting the cyclic nucleotide synthesis in a patient, comprising administering an effective amount of the compound according to claim 1 to said patient.

12. A method of inhibiting the cAMP and cGMP synthesis in a patient, comprising administering an effective amount of the compound according to claim 1 to said patient.

13. A method of treatment of diarrhea, colitis and irritable bowel syndrome in a patient in need thereof, comprising administering an effective amount of the compound according to claim 1 to said patient.

\* \* \* \* \*